United States Patent [19]
Hüttermann et al.

[11] Patent Number: 5,608,040
[45] Date of Patent: Mar. 4, 1997

[54] PROCESS FOR THE PRODUCTION OF LIGNIN-CONTAINING POLYMERS

[75] Inventors: Aloys Hüttermann, Henry-Dunant-Str.20, Gottingen, Germany, 37075; Oleg Milstein, Gottingen, Germany

[73] Assignee: Aloys Hüttermann, Guttingen, Germany

[21] Appl. No.: 436,367

[22] PCT Filed: Sep. 20, 1994

[86] PCT No.: PCT/EP94/03142

§ 371 Date: Jul. 6, 1995

§ 102(e) Date: Jul. 6, 1995

[87] PCT Pub. No.: WO95/08588

PCT Pub. Date: Mar. 30, 1995

[30] Foreign Application Priority Data

Sep. 20, 1993 [DE] Germany .................. 43 31 878.9

[51] Int. Cl.⁶ ............... C08H 5/02; C08F 289/00; C12P 7/22

[52] U.S. Cl. ............... 530/500; 530/501; 530/502; 530/504; 530/505; 435/72; 435/84; 435/100; 435/101; 435/105; 527/400; 527/401; 527/403

[58] Field of Search ................... 530/500, 501, 530/502, 504, 505; 435/72, 84, 100, 101, 105; 527/400, 401, 403

[56] References Cited

PUBLICATIONS

Blinkovsky et al "Peroxidase–Catalyzed Synthesis of Lignin—Phenol Copolymers" Journal of Polymer Science, vol. 31, No. 7, Jun. 1993, pp. 1839–1846.

*Primary Examiner*—Nathan M. Nutter
*Attorney, Agent, or Firm*—Meltzer, Lippe, Goldstein, et al.

[57] ABSTRACT

Polymers containing lignin and organic compounds are produced by polymerizing the lignin with organic compounds containing at least 3 carbon atoms as well as oxygen, nitrogen and/or multiple-linkage functions in the presence of radically oxidizing enzymes and of oxidation products constituting their substrate.

11 Claims, No Drawings

PROCESS FOR THE PRODUCTION OF LIGNIN-CONTAINING POLYMERS

FIELD OF THE INVENTION

The instant invention relates to a process for the production of polymers containing lignin and organic compounds as well as the polymerizates produced in accordance with the process.

BACKGROUND OF THE INVENTION

From U.S. Pat. No. 4,687,828 propene polymers of lignite (2-propene amide)-(Na-2,2-dimethyl-3-imino-4-oxohex-5en-1-sulfonate) and a process for their production are known. Other polymers cannot be produced in this process.

EP-A 91102118.6 discloses propene polymers of lignin and acrylates, e.g. methacrylates. They must be produced in an oxygen-free atmosphere. Only derivatives with acrylates or methacrylates can be produced in this process.

It is the object of the instant invention to create polymers and a process for their production, said polymers consisting of lignin and organic compounds which can be produced in a simple manner and do not require an oxygen-free atmosphere for their production.

SUMMARY OF THE INVENTION

This object is attained through a process for the production of polymers containing lignin and organic compounds wherein the lignin is polymerized with organic compounds containing at least 3 carbons atoms as well as one oxygen and/or nitrogen and/or at least one multiple linkage function in the presence of radical oxidizing enzymes and of oxidation products forming their substrate.

DETAILED DESCRIPTION OF THE INVENTION

In the process according to the invention all organic compounds which contain at least three carbon atoms and at least one oxygen and/or nitrogen atom and/or at least one multiple linkage function can react with lignin. An oxygen-free atmosphere is not required for the process.

The lignin which is used as the initial material may be natural vegetal lignin, e.g., wood. Especially lignin such as results in great quantities from cellulose production, e.g., in form of sulfite lignin or alkali lignin (power lignin) is used. Thereby the instant invention opens a possibility for the utilization of these waste products for which applications were difficult to find in the past.

It has been shown that organic compounds with less than 3 carbon atoms are difficult to polymerize with lignin. Polymerization with acryl derivatives or with organic compounds with 5 or more carbon atoms is especially easy.

The following materials having at least three carbon atoms are especially well suited for polymerization:

Materials with oxygen functions, such as carbonyl compounds, in particular aldehyde and ketone; hydroxyl compounds, in particular monovalent or polyvalent alcohols, ether compounds, in particular mono or poly-ether, and epoxy compounds.

Materials with nitrogen functions, such as amines, imines, amides, amidines, nitriles, isonitriles, and azo compounds.

Materials with at least one multiple linkage function such as e.g., compounds with at least one double and/or triple linkage, preferably with C—C double linkage.

The compounds may also contain several of the functional groups listed above, such as is the case with carbonic acids, carbonic acid anhydrides, acid amides, amidines, carbamides, carbonic acid esters, and peroxides. Other functional groups may also be contained in addition in the compounds, such as is the case with acid halogenides, thio-alcohols, etc.

All the above-mentioned compounds may be in form of aliphatic, aromatic, cyclo-aliphatic or heterocyclic compounds.

The following may be used as radically oxidizing enzymes:

Peroxidases such as manganese peroxidase, radish peroxidase, phenol oxidases such as laccase, and tyrosinases.

In carrying out the polymerization reaction the oxidation products forming the substrate for the enzymes must be present. When peroxidases are used, the oxidation product is hydrogen peroxide, and when phenol oxidases are used, the oxidation product is oxygen. In addition, organic peroxides and organic peroxides and hydroperoxides are suitable substrates. Different enzymes and substrates may be used as mixtures for polymerization.

The reaction may be carried out in aqueous and/or organic solutions or in dispersions formed with such solutions. If organic solutions are used it is preferable if the enzymes are used in the form of enzyme matrix complexes as described in DE 38 27 001Cl.

In the process according to the invention all organic compounds with at least 3 and preferably more than 5 carbon atoms can be polymerized with lignin. Materials with a higher molecular value can also be polymerized, e.g., sugar, starches, cellulose, hemicellulose or derivative of these materials, as well as synthetic polymerizates. Only in instances of stearic impediment can polymerization be hindered.

The lignin used in polymerization is dissolved or reduced to slurry in the solutions used, the copolymer component is added, and the mixture is treated with the enzyme and the co-substrate, e.g., oxygen or hydrogen peroxide is added. When phenol oxidases are used, the oxygen in the air of the reaction chamber is often sufficient to introduce polymerization. The reaction can be carried out at room temperature. At higher temperatures it is accelerated so that it can be carried out within a temperature range of approximately 70° to 80° C., preferably up to approximately 60° C. Furthermore the polymerization reaction can be carried out under adiabatic or isothermal conditions and under increased or reduced pressure. At temperatures above 80° C. the enzyme is generally deactivated. Polymerization is generally complete within a few hours or days.

The invention is explained in further detail below through examples. All indications contained in the examples are considered to be essential to the invention.

EXAMPLE 1

Polymerization of organosolve lignin with glucose:

1 g organosolve lignin with a molecular weight of approximately 6000 was reduced to slurry in 20 ml water and 1 g $C^{14}$-marked glucose was added. A laccase solution was then added until a concentration of 1000 U/ml in the solution was reached. The solution was allowed to polymerize for 4 hours at room temperature.

The constituted polymer was precipitated by setting a pH value of 2 with hydrochloric acid and the obtained precipitate was dissolved in alkali. The precipitation with acid was repeated until the aqueous phase no longer showed any radioactivity.

In the polymerisate obtained glucose was bound covalently to the lignin. The proof was obtained by measuring the radioactivity in the precipitate. For this purpose a gel chromatography of the precipitate was carried out on sephadex LH 20 (exclusion limit 20,000) and the radioactivity of the high-molecular weight fractions was measured. The molecular weight of the co-polymer was above 20,000.

EXAMPLE 2

Polymerization of organosolve liginine with vanillin acid as in Example 1 whereby 1 g organosolve liginine was polymerized with 1g $c^{14}$-marked vanillin acid in dioxane as the solution. The enzyme was used in the form of a matrix complex on destrangel of type sepharose CL 6B.

The polymerisate was characterized as in Example 1.

EXAMPLE 3

Polymerization of organosolve liginine with Sorbit. The polymerisate obtained was characterized as in Example 1.

EXAMPLE 4

Polymerization of organosolve lignin with acrylamide:

0.4 g organosolve lignin were polymerized for 3 hours with 3.2 g acrylamide in dioxane-water 7:3 in the presence of 1000 U/ml laccase. At the beginning of the reaction oxygen was introduced for 20 minutes. The laccase was used as enzyme matrix complex as in Example 2.

The constituted polymerisate was separated by dialysis. The soluble components were precipitated with hydrochloric acid. Two fractions were obtained. One fraction had a molecular weight above 12,000. It consisted of 402 mg polymerisate with an acrylate component of 75.1%. The second fraction consisted of 535 mg polymerisate with a molecular weight over 20,000 and an acrylate component of 14.8%.

We claim:

1. A process for producing a polymer containing lignin which comprises polymerizing lignin with an organic compound, said organic compound containing at least three carbon atoms and at least one oxygen atom, nitrogen atom, or multiple bonds, said organic compound being free from phenolic groups, the polymerization being carried out in the presence of a radical oxidizing enzyme and an oxygen product forming a substrate for the enzyme.

2. The process of claim 1, wherein the radical oxidizing enzyme is selected from the group consisting of peroxidases and phenol oxidases.

3. The process of claim 1, wherein the oxidation product is selected from the group consisting of oxygen and an organic peroxide and organic peroxides and hydroperoxides.

4. The process of claim 3, wherein the organic peroxide is hydrogen peroxide.

5. The process of claim 1, wherein the oxygen atom in the organic compound is contained as a functional group selected from the group consisting of carbonyl, ether, and epoxy.

6. The process of claim 1, wherein the nitrogen atom in the organic compound is contained as a functional group selected from the group consisting of an amine, imine, amide, amidine, nitrile, isonitrile and azo.

7. The process claim 1, wherein the multiple bond in the organic compound contains at least one C—C double or triple bond.

8. The process claim 1, wherein polymerization is carried out at a temperature of from about 70° to 80° C.

9. The process of claim 1, wherein the polymerization is carried out at a temperature of up to about 60° C.

10. A process for producing a polymer containing lignin which comprises polymerizing lignin with an organic compound, said organic compound containing at least three carbon atoms and at least one of a carbonyl, ether or epoxy functional group, a nitrogen atom or multiple bonds, the polymerization being carried out in the presence of a radical oxidizing enzyme and an oxygen product forming a substrate for the enzyme.

11. A polymer produced by the process of claim 1.

* * * * *